United States Patent [19]

Ishida

[11] Patent Number: 5,289,717
[45] Date of Patent: Mar. 1, 1994

[54] AIR-FUEL RATIO DETECTING DEVICE
[75] Inventor: Tetsurou Ishida, Kyoto, Japan
[73] Assignee: Mitsubishi Jidosha Kogyo kabushiki Kaisha, Tokyo, Japan
[21] Appl. No.: 731,006
[22] Filed: Jul. 16, 1991
[30] Foreign Application Priority Data
 Jul. 20, 1990 [JP] Japan .................. 2-193583
[51] Int. Cl.$^5$ ............................. G01M 15/00
[52] U.S. Cl. ......................... 73/117.3; 73/46; 73/23.2
[58] Field of Search ............. 73/23.2, 116, 117.3; 436/136, 137, 138; 204/406; 123/492, 494
[56] References Cited

U.S. PATENT DOCUMENTS 3,948,081 4/1976 Wessel et al. ............ 73/23.32
4,488,529 12/1984 Nishida et al. ............ 123/492

FOREIGN PATENT DOCUMENTS 63-36140 2/1988 Japan .

Primary Examiner—Robert Raevis

[57] ABSTRACT

An air fuel ratio detecting device has an air-fuel ratio sensor for producing an air-fuel ratio information indicative of the concentration of oxygen in an exhaust gas produced by a burned air-fuel mixture in the internal combustion engine. An air-fuel ratio is calculated on the basis of the air-fuel ratio information. A pressure in the exhaust gas is calculated on the basis of pressure information depending on the pressure of the exhaust gas. The difference between the pressure and a reference pressure which acts on the air-fuel ratio sensor when the air-fuel ratio sensor is placed in a reference environment, is calculated. The air-fuel ratio is corrected with the pressure difference. The corrected air-fuel ratio is free of pressure fluctuations of the exhaust gas, and is highly reliable for accurate air-fuel ratio control. The air-fuel ratio detecting device is effective for improved fuel economy, increased engine output power, a more stable idling engine speed, purified exhaust emission, and improved drivability.

30 Claims, 8 Drawing Sheets

PROCESSING BY
AIR-FUEL RATIO
DETECTING DEVICE $\Delta P \leftarrow P_K - P_0$ $S_0 \leftarrow G \times S_S \times \Delta P$ $A/F \leftarrow S_0$

TURN ON STARTER SW

STARTER FLAG=1

END

AIR-FUEL RATIO DETECTING DEVICE

BACKGROUND OF THE INVENTION

1. Field of the Invention

The present invention relates to an air-fuel ratio detecting device for detecting the air-fuel ratio (A/F) of an air-fuel mixture to be supplied to an internal combustion engine.

2. Related Art

There has been proposed a linear A/F sensor utilizing the oxygen concentration cell capability and oxygen ion pumping capability of zirconia, for detecting whether the air-fuel ratio is on a leaner or richer side of a stoichiometric ratio and also for detecting the value of the air-fuel ratio (see Japanese Laid-Open Patent Publication No. 63(1988)-36140).

One conventional linear A/F sensor will be described below with reference to FIGS. 7 through 10 of the accompanying drawings. FIG. 7 shows a linear A/F sensor including a sensor cell 20 and a pump cell 21 which are shown detached from each other, and each includes a stabilized zirconia device. The sensor cell 20 and the pump cell 21 are coupled to each other through an insulation layer 22. The sensor cell 20 and the pump cell 21 have respective diffusion holes 23, 24 defined therein for passing therethrough exhaust gases from an internal combustion engine. The insulation layer 22 has a detecting cavity 25 defined therein into which exhaust gases can be introduced through the diffusion holes 23, 24 by the sensor cell 20 and the pump cell 21. The diffusion holes 23, 24 and the detecting cavity 25 jointly serve as an element for controlling the speed at which the exhaust gases are diffused. The insulation layer 22 also has a reference chamber 25a positioned below the detecting cavity 25 in spaced-apart relation thereto, with the reference chamber 25a being defined between the sensor cell 20 and the pump cell 21. A reference gas such as atmospheric air is introduced into the reference chamber 25a through a communication hole (not shown). As shown in FIG. 8, the sensor cell 20 has porous electrodes 26, 27 of platinum, and the pump cell 21 has porous electrodes 28, 29 of platinum, with the electrodes 26, 27, 28, 29 doubling as a catalyst. The sensor cell 20 has an electric heater 30 for heating itself to a temperature range, e.g., 800°±100° C. in order to keep the sensor cell 20 active.

The sensor cell 20 functions as a conventional $O_2$ sensor for developing an electromotive force if there is an oxygen concentration difference between the electrodes 26, 27. The pump cell 21 also has the same properties as the sensor cell 20, and serves to pump oxygen from a negative electrode to a positive electrode when an electric current (pump current Ip) is caused to flow between the electrodes 28, 29.

A control assembly 31 detects an electromotive force Vs developed by the sensor cell 20, and also controls the pump current Ip through a feedback loop in order to keep constant the electromotive force Vs, i.e., in order to keep an oxygen concentration corresponding to a stoichiometric ratio in the detecting cavity 25 or the diffusion holes 23, 24. Since the pump current Ip continuously varies with respect to the air-fuel ratio, as shown in FIG. 9, the air-fuel ratio can be calculated from the pump current Ip.

More specifically, the control assembly 31 includes a comparator 1 and an integrator amplifier 2 with positive and negative power supplies. The comparator 1 compares the electromotive force Vs and a reference voltage Vref corresponding to the stoichiometric ratio. The output signal from the comparator 1 is integrated by the integrator amplifier 2, whose integral output signal is applied as the pump current Ip to the pump cell 21 through a resistor 5. At this time, a voltage drop across the resistor 5 is detected by a current detector 3 which produces a voltage signal commensurate with the pump current Ip. Therefore, the pump current Ip is detected indirectly by the current detector 3. The output signal of the current detector 3 is applied to an adder 4 which then produces an output signal Vout, in the range of from 0 to 5 volts, representing the air-fuel ratio, according to the following equation:

$$Vout = G.Ip + Vstp$$

where G is the current-to-voltage conversion gain of a current-to-voltage converter which is composed of the resistor 5 and the current detector 3, and Vstp is a step-up voltage in the range of from 0 to 5 volts.

In the conventional system shown in FIG. 8, the voltage drop across the resistor 5 is applied to a current inversion detector 6 to detect the direction in which the pump current flows, for thereby producing a stoichiometric air-fuel ratio Vstc (see FIG. 10).

With the linear A/F sensor, the pump current Ip is of a value corresponding to the concentration of $O_2$ (which, if higher, makes the air-fuel mixture leaner) in the exhaust gas, and the concentrations of $H_2$, CO (which, if higher, make the air-fuel mixture richer), and has a characteristic as indicated by the following equation (1):

$$Ip \propto (K_1.T^{0.75}.S/L + K_2.T^{-0.5}.Pg.S/L) \qquad (1)$$

where $K_1$ and $K_2$ are constants that vary depending on the structure of the linear A/F sensor, T the absolute temperature, Pg the partial pressure of oxygen in the measured exhaust gas, S the cross-sectional area of the diffusion hole in the gas diffusion limiting layer, and L the thickness of the gas diffusion limiting layer.

It is known that if the linear A/F sensor is of such a structure as to mainly diffuse the gas with molecules, then the constant $K_1$ is larger than the constant $K_2$, making the air-fuel ratio information highly dependent on the temperature, and if the linear A/F sensor is of such a structure as to mainly diffuse the gas with minute holes, then the constant $K_2$ is larger than the constant $K_1$, making the air-fuel ratio information highly dependent on the pressure.

In the case where the linear A/F sensor of a structure to mainly diffuse the gas with minute holes is employed, it has been found that, as shown in FIG. 9, the pump current vs. air-fuel ratio curve b which is plotted under a reference pressure acting on the sensor in a reference environment widely deviates from the pump current vs. air-fuel ratio curve a which is plotted under a measured pressure on the sensor on both sides of the stoichiometric air-fuel ratio (where the pump current Ip is zero), with the deviation being greater as the absolute value of the pump current Ip is greater.

With the linear A/F sensor which is of a structure to mainly diffuse the gas with minute holes, no consideration has heretofore been given to the dependency of the air-fuel ratio information produced by the sensor, on the pressure and temperature. It has been customary to control the air-fuel ratio of the fuel injection device through a feedback control loop based on the air-fuel ratio information which is not corrected.

Accurate control of the air-fuel ratio so that it reaches a target value while the internal combustion engine is in operation is very important for improved fuel economy, increased engine output power, stabler idling engine speed, purified exhaust emission, and improved drivability. However, the above conventional air-fuel ratio control process has proven unsatisfactory.

SUMMARY OF THE INVENTION

It is an object of the present invention to provide an air-fuel ratio detecting device for detecting the air-fuel ratio of an air-fuel mixture highly and reliably through correction of the air-fuel ratio based on the pressure in an exhaust pipe, for thereby allowing the air-fuel ratio to be subsequently controlled highly and accurately for improved fuel economy, increased engine output power, stabler idling engine speed, purified exhaust emission, and improved drivability.

According to the present invention, there is provided an air-fuel ratio detecting device for an internal combustion engine, comprising an air-fuel ratio sensor for producing an air-fuel ratio information indicative of the concentration of oxygen in an exhaust gas produced by a burned air-fuel mixture in the internal combustion engine, exhaust pressure calculating means for calculating a pressure in the exhaust gas, pressure difference calculating means for calculating the pressure difference between the pressure and a reference pressure which acts on the air-fuel ratio sensor to cause the air-fuel ratio sensor to have reference output characteristics when the air-fuel ratio sensor is placed in a reference atmosphere, and air-fuel ratio calculating means for calculating an air-fuel ratio based on the air-fuel ratio information and correcting the air-fuel ratio with the pressure difference calculated by the pressure difference calculating means for thereby producing a pressure-corrected air-fuel ratio.

The air-fuel ratio information from the air-fuel ratio sensor is corrected depending on the pressure in the exhaust pipe of the engine, for correcting the air-fuel ratio so as to correspond to the reference pressure.

Since the corrected air-fuel ratio is maintained highly and accurately at a target air-fuel ratio, the air-fuel ratio detecting device is effective for improved fuel economy, increased engine output power, stabler idling engine speed, purified exhaust emission, and improved drivability.

The above and other objects, features, and advantages of the present invention will become apparent from the following description when taken in conjunction with the accompanying drawings which illustrate preferred embodiments of the present invention by way of example.

DETAILED DESCRIPTION OF THE PREFERRED EMBODIMENTS

Figure 1:
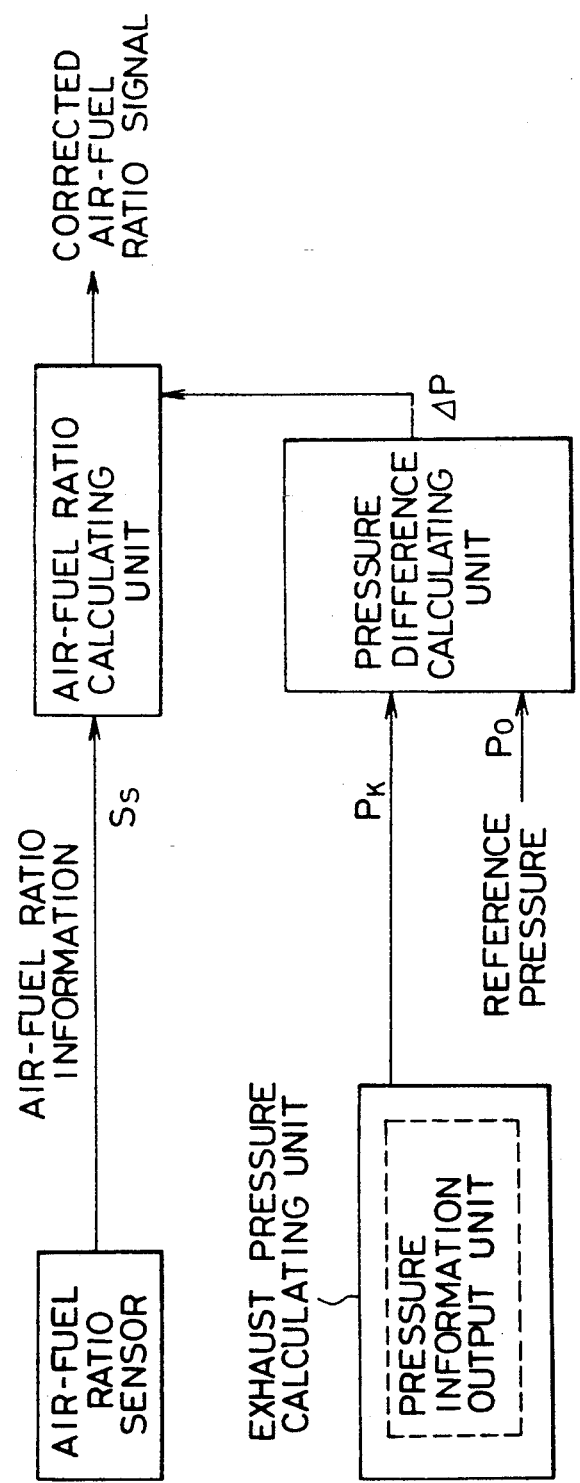
FIG. 1 is a schematic block diagram of an air-fuel ratio detecting device according to an embodiment of the present invention.

FIG. 1 shows in block form an air-fuel ratio detecting device according to an embodiment of the present invention.

As shown in FIG. 1, the air-fuel ratio detecting device has an air-fuel ratio sensor for outputting air-fuel ratio information Ss (corresponding to the air-fuel ratio signal Vout in FIG. 8) representing the air-fuel ratio detected in the exhaust pipe of an internal combustion engine, a pressure information output unit disposed near the air-fuel sensor, for detecting the pressure of an exhaust gas in which the air-fuel sensor is placed, an exhaust pressure calculating unit for calculating an exhaust pressure Pk from a predetermined map or the like depending on the pressure information from the pressure information output unit, a pressure difference calculating means for calculating the difference $\Delta P$ between the exhaust pressure Pk and a reference pressure Po, and an air-fuel ratio calculating unit for correcting the air-fuel ratio information Ss with the pressure difference $\Delta P$ and outputting a corrected air-fuel ratio signal.

The corrected air-fuel ratio signal is supplied to a feedback control system employing the corrected air-fuel ratio signal, e.g., the fuel injection control system of an internal combustion engine.

Figure 2:
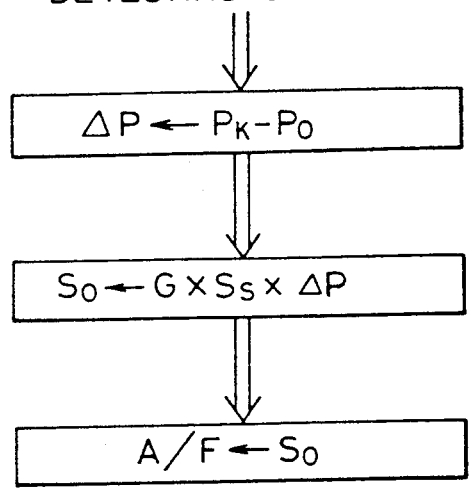
FIG. 2 is a flowchart of a process of correcting an air-fuel ratio produced by an air-fuel sensor with the air-fuel ratio detecting device.

FIG. 2 shows a processing sequence carried out by the air-fuel ratio detecting device shown in FIG. 1. According to the processing sequence, the pressure difference $\Delta P$ between the exhaust pressure Pk outputted from the exhaust pressure calculating unit and the reference pressure Po in a reference environment is first calculated. Then, the air-fuel ratio information Ss from the air-fuel ratio sensor is corrected. Specifically, the pressure difference $\Delta P$ (=Pk−Po) is multiplied by a corrective constant G, and the air-fuel ratio information Ss from the air-fuel ratio sensor is corrected by a corrective Ss that depends on the pressure difference $\Delta P$, for producing pressure-corrected air-fuel ratio information So. Thus, the pressure-corrected air-fuel ratio information So is calculated according to the following equation (2):

$$So = G \times (Pk - Po) \times SS \qquad (2)$$

Figure 9:
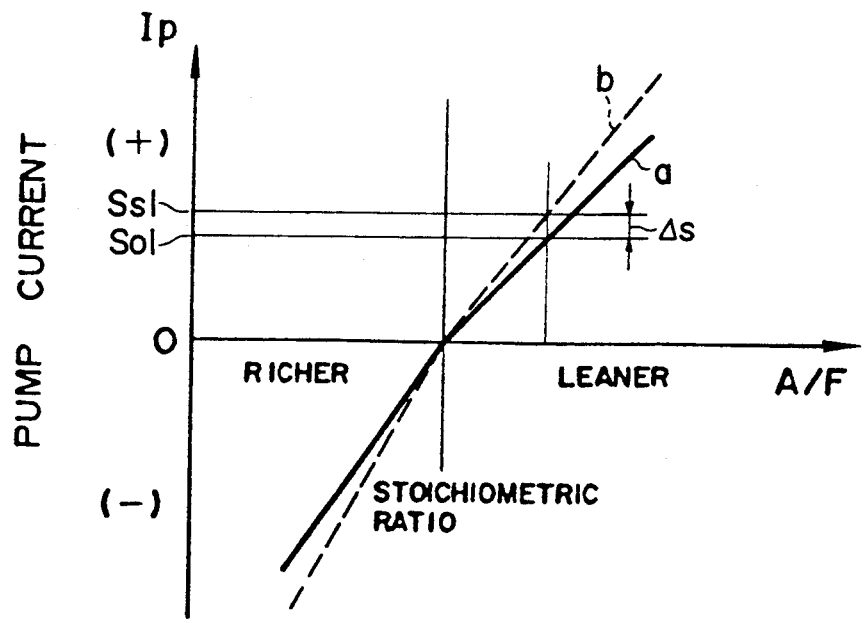
FIG. 9 is a diagram showing the relationship between a pump current and an air-fuel ratio.
Figure 10:
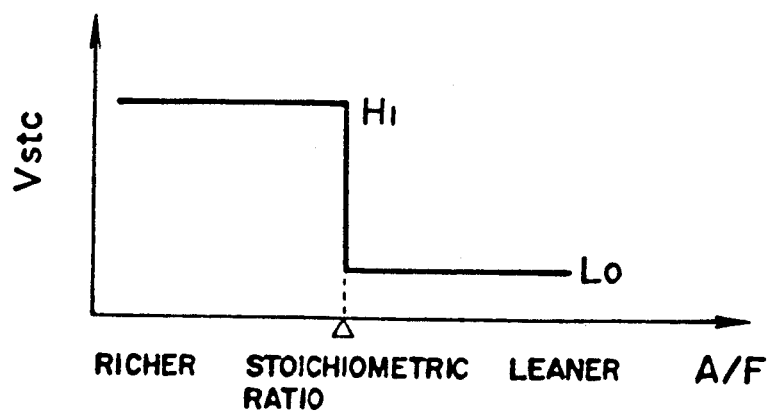
FIG. 10 is a diagram showing a stoichiometric ratio signal with its level depending on the direction of the pump current.

For example, the pump current vs. air-fuel ratio curve b shown in FIG. 9 may be corrected by the above processing sequence as follows. Air-fuel ratio information Ss1 on the curve b is corrected by the pressure corrective $\Delta S$ into corrected air-fuel ratio information So1 on the pump current vs. air-fuel ratio curve a, for thereby producing an air-fuel ratio under the reference pressure.

Figure 3:
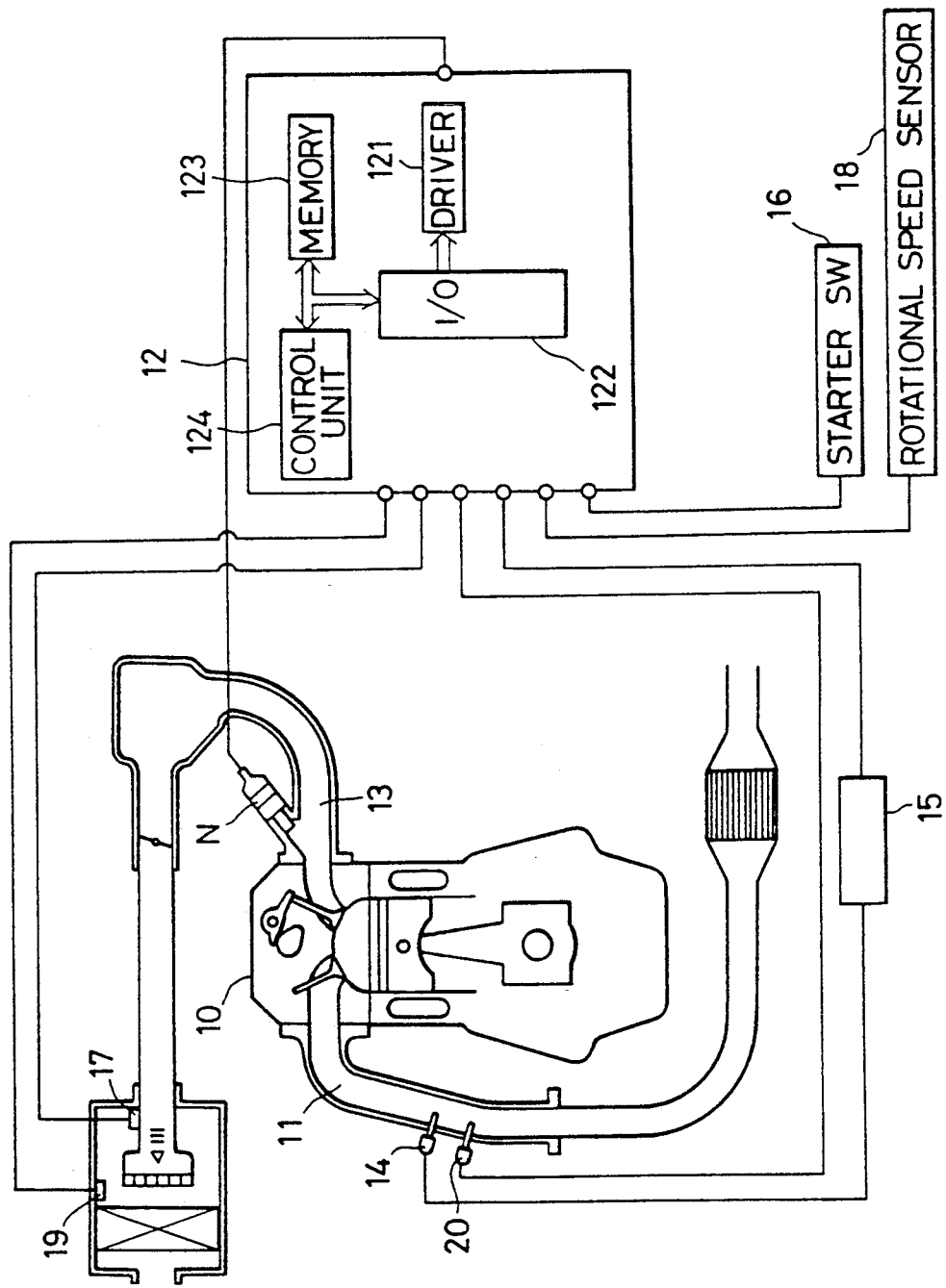
FIG. 3 is a block diagram, partly in cross section, of a fuel injection control system in which the process of correcting an air-fuel ratio shown in FIG. 2 can be effected.

FIG. 3 shows a fuel injection control system for an internal combustion engine. The process of correcting an air-fuel ratio shown in FIG. 2 can be effected in the fuel injection control system.

As shown in FIG. 3, the fuel injection control system includes a linear A/F sensor 14 disposed in an exhaust passage 11 of an internal combustion engine 10. Air-fuel ratio (A/F) information Ss produced by the linear A/F sensor 14 is outputted to an engine controller 12. The engine controller 12 then calculates a rate of fuel to be supplied to the engine 10 based on the air-fuel ratio information Ss. The fuel injection control system includes a fuel injection nozzle N for injecting the calculated rate of fuel into an intake passage 13 of the engine 10.

Figures 7, 8:
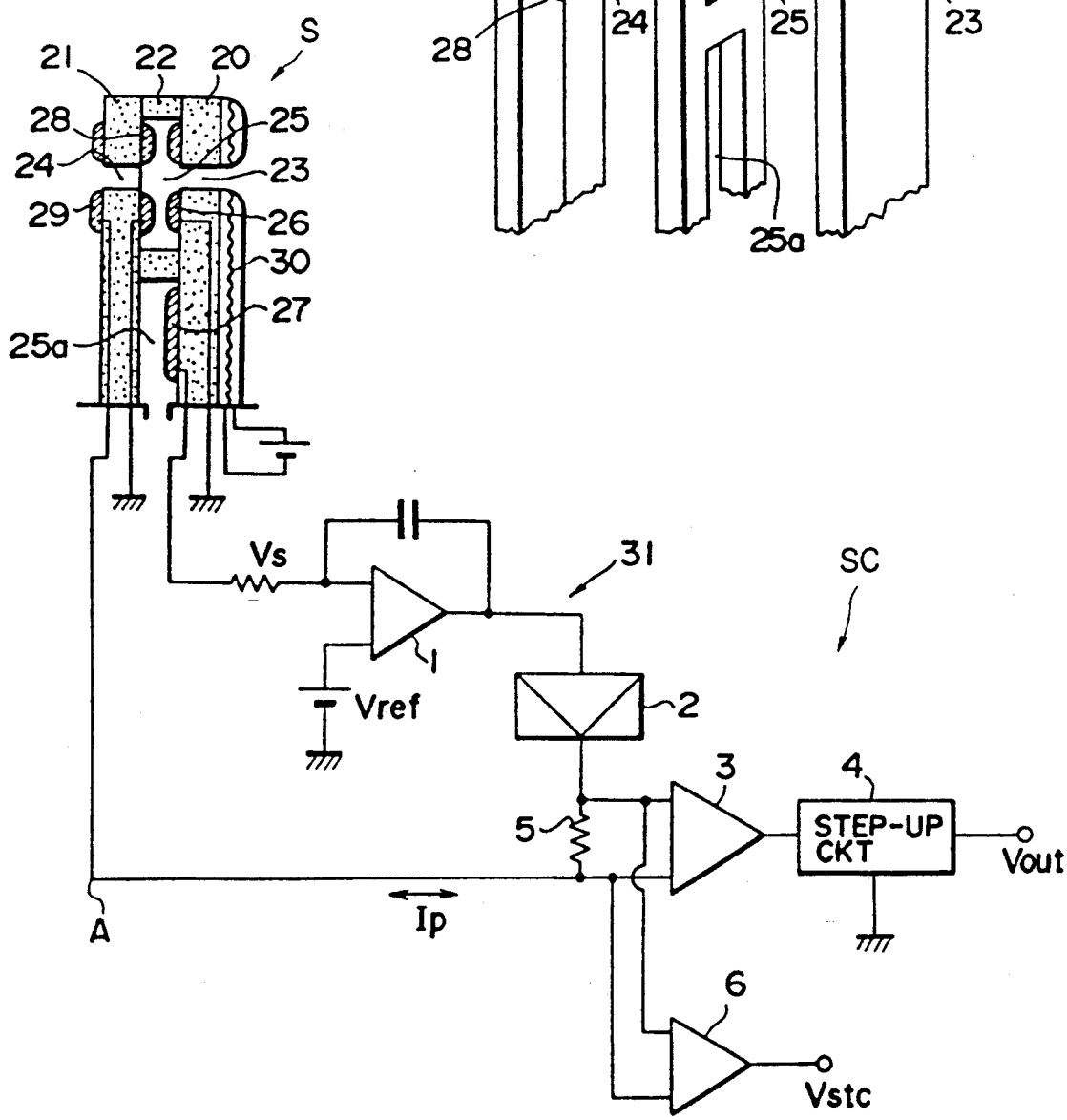
FIG. 7 is an exploded perspective view of a conventional air-fuel ratio sensor.
FIG. 8 is a schematic view, partly in block form, of the conventional air-fuel ratio sensor shown in FIG. 7.

The linear A/F sensor 14 and a control assembly 15 therefor shown in FIG. 3 are of the same arrangement as the linear A/F sensor and the control assembly 31 of the conventional system shown in FIG. 8, and will not be described in detail.

In FIG. 3, the linear A/F sensor 14 and the control assembly 15 therefor make up the air-fuel ratio sensor (see FIG. 1). The linear A/F sensor 14 is connected to the engine controller 12 through the control assembly 15, and applies an air-fuel ratio signal Ss, in the range from 0 to 5 volts, to the engine controller 12.

A starter switch 16 is disposed in a combination switch assembly (not shown) of the engine, and applies an ON or OFF signal to the engine controller 12. An air flow sensor 17 applies a signal indicative of intake air rate information to the engine controller 12. An engine rotational speed sensor 18 applies a signal indicative of engine rotational speed information to the engine controller 12. An atmospheric pressure sensor 19 applies a signal indicative of atmospheric pressure information to the engine 12. A pressure sensor 20, as the pressure information output unit (see FIG. 1), outputs exhaust pressure information to the engine controller 12. The pressure sensor 20 is disposed in the exhaust passage 11 in the vicinity of the linear A/F sensor 14.

Figure 4C:
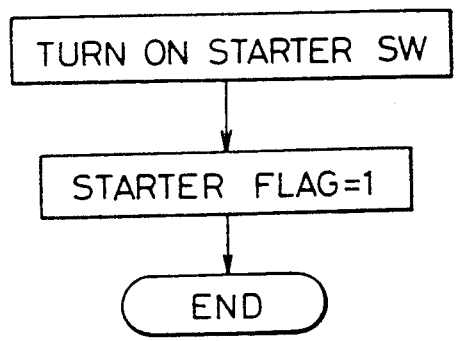
FIGS. 4(a) through 4(c) are flowcharts of an air-fuel ratio control program which is executed by a controller in the fuel injection control system shown in FIG. 3.
Figure 4A:
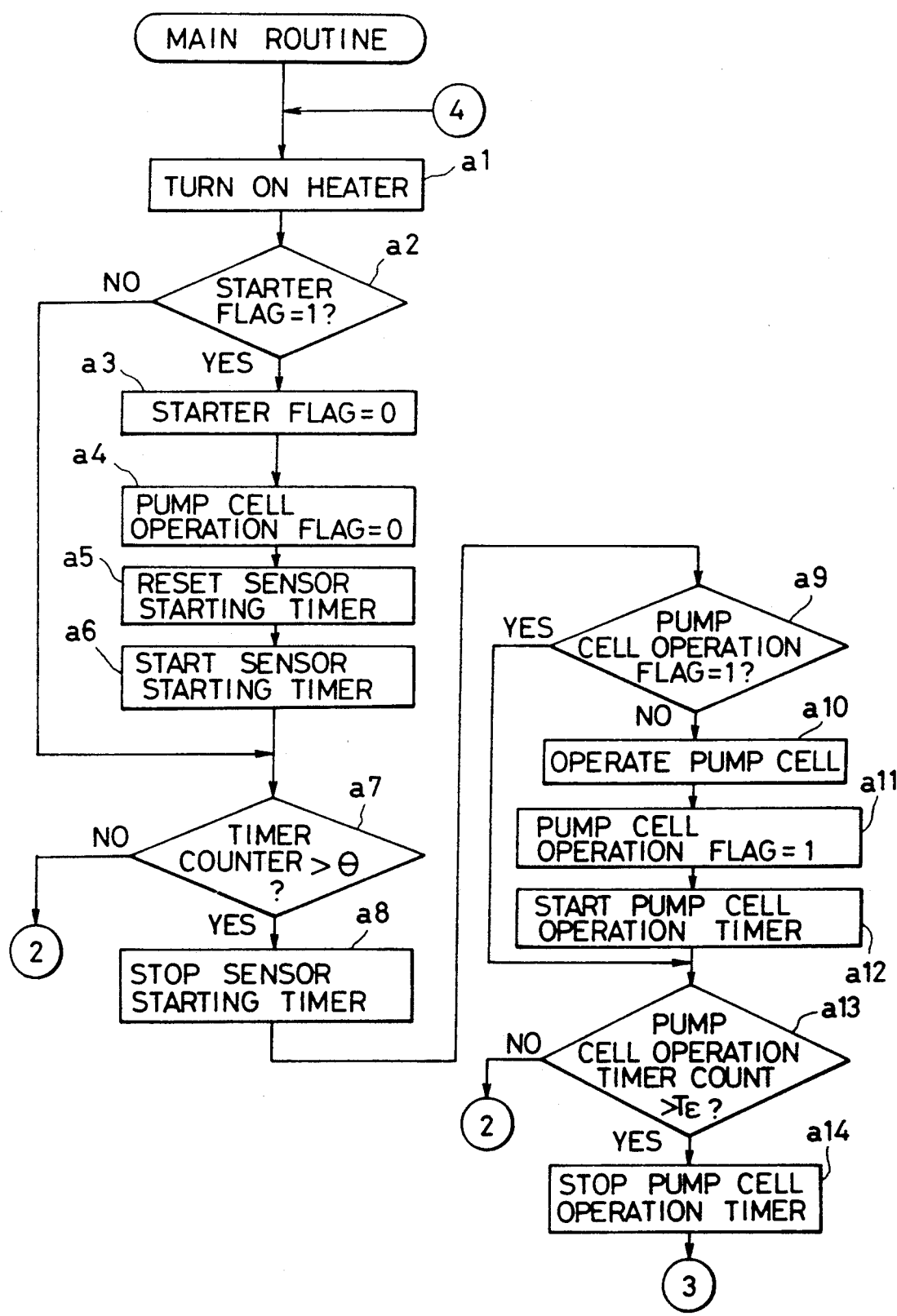
Figure 4B:
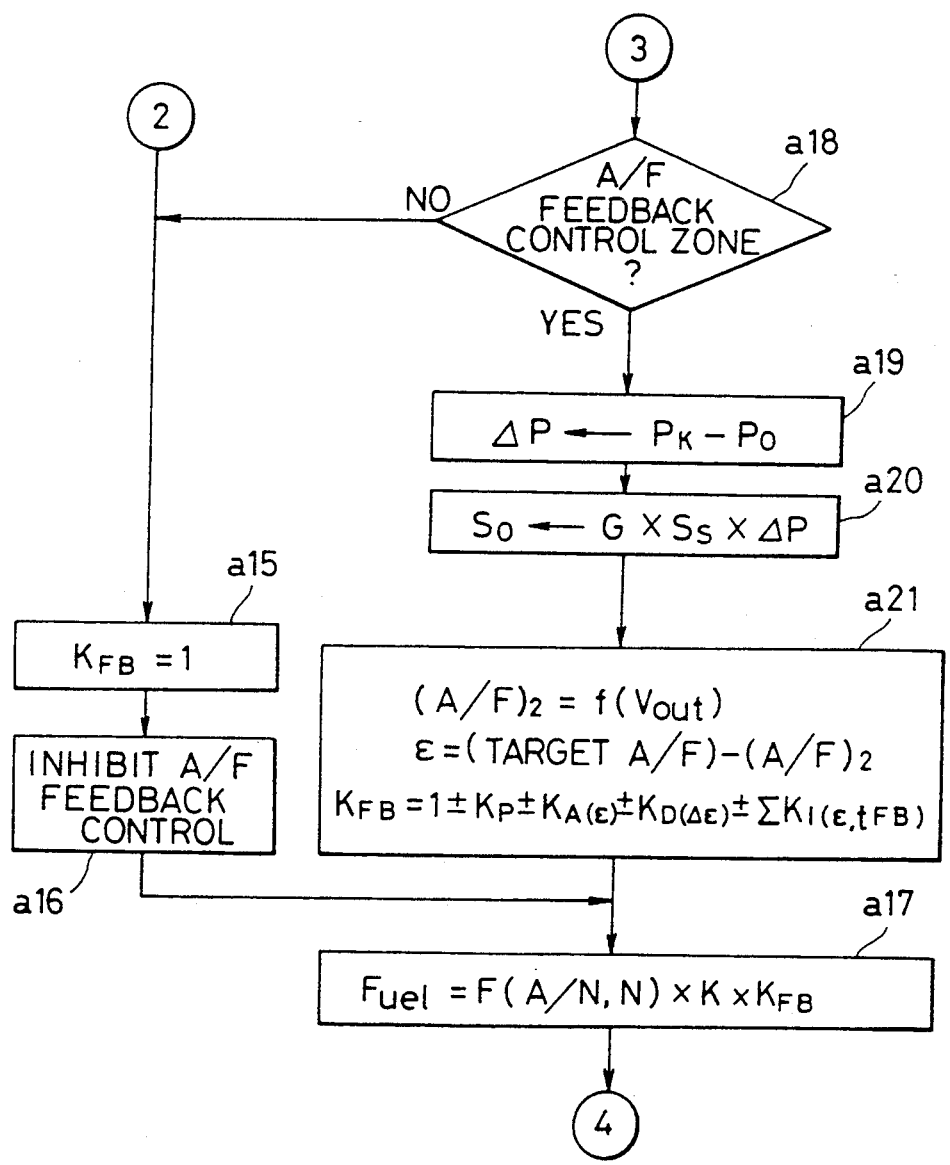

The engine controller 12 is mainly composed of a microcomputer, and includes a driver 121 for actuating the fuel injection nozzle N, an input/output interface 122 for receiving various output signals and applying a control signal to the driver 121, a memory 123 which stores a control program for controlling the air-fuel ratio (see FIGS. 4(a) through 4(c)), and a control unit 124 for calculating control values according to the control program.

The functions of the engine controller 12, i.e., the exhaust pressure calculating unit, the pressure difference calculating unit, and the air-fuel ratio calculating unit, will be described below. In addition to those functions, the engine controller 12 also has a fuel rate injection controller for controlling the rate of fuel to be injected through feedback control based on the corrected air-fuel ratio.

A process of correcting an air-fuel ratio from the air-fuel ratio sensor will be described with reference to the control program shown in FIGS. 4(a) through 4(c). The air-fuel ratio correcting process is carried out simultaneously with a process of controlling the rate of fuel to be injected (through air-fuel ratio feedback control and air-fuel ratio open-loop (non-feedback) control) with the engine controller 12.

The control program has a main routine shown in FIGS. 4(a) and 4(b) which starts to be executed by the engine controller 12 when the starter switch 16 is turned on. When the starter switch 16 is turned on, a starter flag is set, as shown in FIG. 4(c). In the main routine, a heater 30 (see FIG. 8) is turned on in a step a1, which is followed by a step a2 that determines whether the starter flag is 1 or not. If the starter flag is not 1, then control jumps to a step a7, and if the starter flag is 1, then control proceeds to a step a3.

The starter flag is cleared to 0 in the step a3, and a pump cell operation flag that allows the pump current Ip (see FIG. 9) to be supplied is cleared in a step a4. In a step a5, a sensor starting timer is reset which defines a time to start the linear A/F sensor 14. Thereafter, the sensor starting timer is started in a step a6.

A next step a7 determines whether the count of the sensor starting timer exceeds a preset value $\theta$ which has been set to an interval of a time long enough for the air-fuel ratio sensor to be activated while the engine 10 is being warmed up. If the count of the sensor starting timer does not exceed the preset value $\theta$, then control goes to a step a15 in which an air-fuel ratio feedback control coefficient $K_{FB}$ is set to 1. Then, the air-fuel ratio feedback control process is inhibited in a step a16. Then, control proceeds to a step a17 in which a fuel injection rate Fuel is calculated. Specifically, a rate of fuel to be injected is determined from a predetermined map depending on the engine rotational speed N and the engine load A/N, and the determined fuel injection rate Fuel is stored in a predetermined memory area. Stated otherwise, the open-loop process for controlling the rate of fuel to be injected is carried out in the step a17. Thereafter, control returns from the step a17 to the step al of the main routine. In a fuel injection routine (not shown) subsequent to the above process, the rate of fuel to be injected is determined in response to an interrupt at a certain crankshaft angle, and fuel is ejected at the determined rate to achieve a target air-fuel ratio determined by the air-fuel ratio open-loop control process.

If the count of the sensor starting timer exceeds the preset value $\theta$ in the step a7, then control proceeds to a step a8. In the step a8, if the sensor starting timer is still in operation, the counting operation thereof is stopped while retaining the count achieved so far. Then, control goes from the step a8 to a step a9.

The step a9 determines whether the pump cell operation flag is 1 or not. If the pump cell operation flag is not 1, then control proceeds to a step a10 in which the pump cell 21 is operated. Then, the pump cell operation flat is set to 1 in a step a11, which is followed by a step a12 in which a pump cell operation timer is started. A step a13 determines whether the count of the pump cell operation timer exceeds a preset value T $\epsilon$ which has been set to an interval of a time long enough for the output signal of the air-fuel ratio sensor to be stabilized. If the count of the pump cell operation timer does not exceed the preset value $\epsilon$, then control goes to the step a15 for continuing the open-loop control process. If the count of the pump cell operation timer exceeds the preset value $\epsilon$, i.e., if the sensor output becomes stable and the pump current Ip becomes reliable, then control goes from the step a13 to a step a14. In the step a14, if the pump cell operation timer is still in operation, the counting operation thereof is stopped while retaining the count achieved so far. Then, control goes from the step a14 to a step a18.

The step a18 determines whether the present operating conditions of the engine fall within an air-fuel ratio feedback control range or not. If the present operating conditions are not in the air-fuel ratio feedback control range, then control goes to the step a15 for the air-fuel ratio open-loop control process.

If the present operating conditions of the motor vehicle are in the air-fuel ratio feedback control range in the step a18, then control goes to a step a19. In the step a19, the exhaust pressure calculating unit reads the pressure in the exhaust pipe as detected by the pressure sensor 20, and calculates a pressure Pk on the linear A/F sensor 14 from the read pressure. In the step a19, the pressure difference calculating unit calculates the pressure difference $\Delta P$ between the pressure Pk and a reference pressure Po on the linear A/F sensor 14. Then, the air-fuel ratio information Ss from the air-fuel ratio sensor is corrected by the pressure difference $\Delta P$ according to the equation (2) above in a step a20, for providing corrected air-fuel ratio information So.

Thereafter, control proceeds from the step a20 to a step a21. The step a21 calculates an actual air-fuel ratio $(A/F)_2$ based on the corrected air-fuel ratio information So according to the equation: $(A/F)_2 = f(So)$. Then, a target air-fuel ratio A/F that has already been determined depending on operating conditions of the motor vehicle which incorporates the engine with the air-fuel ratio detecting device is read, and an error or difference $\epsilon$ between the read target air-fuel ratio A/F and the actual air-fuel ratio $(A/F)_2$ is calculated, and so is a difference $\Delta\epsilon$ between the presently calculated error $\epsilon$ and the previously calculated error. Finally in the step a21, a corrective coefficient $K_{FB}$ is calculated for the control of a fuel injection rate based on the air-fuel ratio.

The corrective coefficient $K_{FB}$ is calculated as the sum of, or difference between, a proportional term $KA(\epsilon)$ of a gain depending on the level of the error $\epsilon$, an offset Kp for the prevention of a response delay owing to the three-way catalytic converter, a differential term $K_{D(\Delta\epsilon)}$ depending on the difference $\Delta\epsilon$, an integral term $\Sigma K_{I(\epsilon, tFB)}$, and 1.

Thereafter, Control goes to the step a17 in which a proper rate of fuel to be supplied at the time is calculated from the corrective coefficients $K_{FB}$, K, and the basic fuel injection rate F(A/N,N). Control then returns to the step a1 in the main routine.

The rate of fuel to be supplied which is thus determined in the routine shown in FIGS. 4(a) and 4(b) is called in the fuel injection routine that is executed at the time of an interrupt effected in response to a crankshaft angle signal produced in the main routine. The fuel injection nozzle N is then actuated by the driver 121 for an interval of time corresponding to the determined rate of fuel to be supplied, for thereby injecting fuel at the rate which achieves the desired air-fuel ratio.

In the above embodiment, the pressure information from the pressure sensor 20 as the pressure information output unit is read by the exhaust pressure calculating unit. However, the pressure information may be produced in another way.

Figure 5:
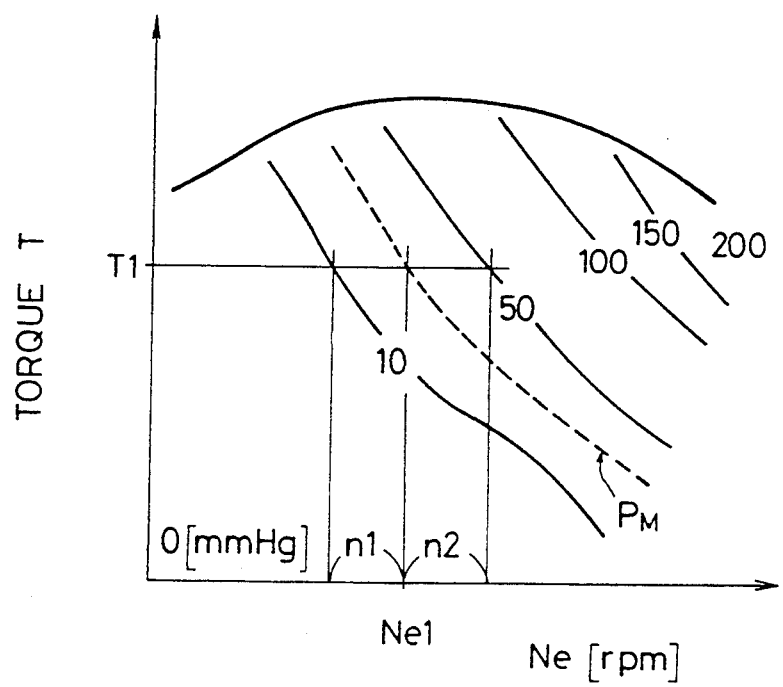
FIG. 5 is a diagram showing a map of engine torques, engine speeds, and exhaust pressures.

For example, the pressure information output unit may be composed of the engine rotational speed sensor 18 and the air flow sensor 17, and pressure information in the exhaust pipe may be obtained on the basis of the engine rotational speed and the amount of intake air that has been drawn into the intake pipe. More specifically, the memory 123 of the controller 12 stores a three-dimensional map of engine rotational speeds Ne, engine torques T, and exhaust pressures $P_M$, as shown in FIG. 5, with the map serving as the exhaust pressure calculating unit. First, the engine rotational speed Ne and the amount A of intake air are detected, the rate A/N of intake air is then calculated from the engine rotational speed Ne and the amount A of intake air, and the engine torque T is calculated from the rate A/N of intake air and the engine rotational speed Ne. Thereafter, the exhaust pressure $P_M$ depending on the engine rotational speed Ne and the engine torque T is determined from the three-dimensional map shown in FIG. 5. If no exact exhaust pressure data is available on the map, then such data is interpolated between closest points on the map. For example, exhaust pressure data at the engine rotational speed Ne1 and the engine torque T1 in FIG. 5 can be interpolated as follows: $\{n1/(n1+n2)\} \times (50-10) + 10 = P_M$.

Then, the atmospheric pressure $P_A$ is read from the atmospheric pressure sensor 19, and a pressure Pk $(=P_M+P_A)$ is calculated. The pressure Pk thus determined is employed in the step a19 of the main routine. If the atmospheric pressure sensor 19 is not present, then the pressure $P_M$ may be used as the pressure Pk.

In the case where the pressure information output unit is composed of the engine rotational speed sensor and the air flow sensor, the pressure sensor 20 may be dispensed with, and hence the number of parts used may be reduced.

If the map shown in FIG. 5 is not available, then the atmospheric pressure $P_A$ may be read from the atmospheric pressure sensor 19, the pressure Pk $(=P_A)$ may be calculated, and then the pressure Pk may be employed in the step a19 of the main routine.

Figure 6:
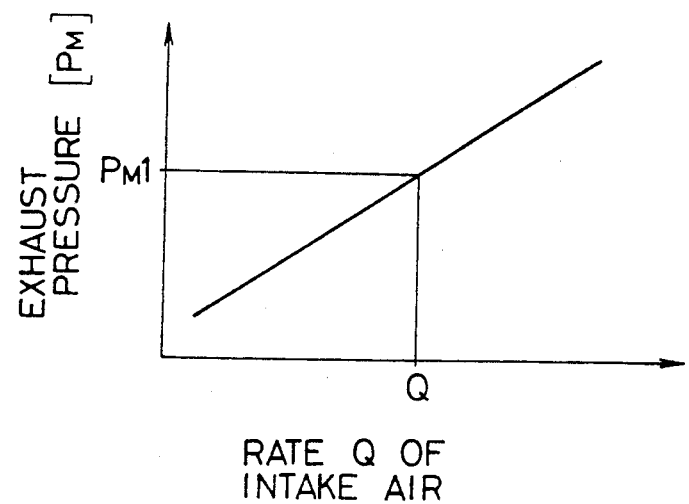
FIG. 6 is a diagram showing a map of exhaust pressures and amounts of intake air.

Alternatively, the pressure information output unit may include the air flow sensor 17. More specifically, the memory 123 of the engine controller 12 stores a map of rates Q of intake air and exhaust pressures $P_M$ in the exhaust passage, as shown in FIG. 6, with the map serving as the exhaust pressure calculating unit. The engine controller 12 determines the rate Q of intake air (=A/N) from the engine rotational speed Ne and the amount A of intake air, determines an exhaust pressure $P_M1$ from the map according to the intake air rate Q, and calculates pressure information Pk $(=P_M1)$. The correlation between intake air rates Q $(=A/N)$ and exhaust pressures $P_M1$ in the exhaust passage is experimentally determined.

If the engine controller 12 is associated with the atmospheric pressure sensor 19, then the exhaust pressure $P_M1$ may be determined from the map shown in FIG. 6, the atmospheric pressure $P_A$ may be read from the atmospheric pressure sensor 19, the pressure information Pk $(=PA+PM1)$ may be calculated, and the pressure information Pk may be employed in the step a19 of the main routine.

Although certain preferred embodiments of the present invention have been shown and described in detail, it should be understood that various changes and modifications may be made therein without departing from the scope of the appended claims.

What is claimed is:

1. An air-fuel ratio detecting device, comprising:
   an air-fuel ratio sensor for producing air-fuel ratio information indicative of the concentration of oxygen in an exhaust gas produced by a burned air-fuel mixture in an internal combustion engine, said air-fuel ratio sensor being disposed in an exhaust pipe;

operating status data detecting means for detecting engine operating parameters indicative of or corresponding to a pressure in the exhaust gas;

pressure difference calculating means for calculating the pressure difference between a first pressure which acts on said air-fuel ratio sensor to cause the air-fuel ratio sensor to have reference output characteristics when the air-fuel ratio sensor is placed in a reference atmosphere and a second pressure which is indicative of or corresponding to said pressure in the exhaust gas detected by said operating status detecting means; and air-fuel ratio calculating means for correcting an air-fuel ratio based on said air-fuel ratio information from said air-fuel ratio sensor with the pressure difference calculated by said pressure difference calculating means, for thereby producing a pressure-corrected air-fuel ratio.

2. An air-fuel ratio detecting device according to claim 1, wherein said air-fuel ratio sensor is of a structure for mainly diffusing the exhaust gas with minute holes.

3. An air-fuel ratio detecting device according to claim 2, wherein said operating status data detecting means comprises a pressure sensor for detecting pressure information indicative of the exhaust pressure.

4. An air-fuel ratio detecting device according to claim 3, wherein said air-fuel ratio sensor is disposed in the exhaust pipe so as to directly detect the exhaust pressure, and wherein the pressure information obtained by said pressure sensor corresponds to said second pressure.

5. An air-fuel ratio detecting device according to claim 3, wherein said pressure sensor comprises an atmospheric pressure sensor for detecting an atmospheric pressure, and the atmospheric pressure obtained by said atmospheric pressure sensor corresponds to said second pressure.

6. An air-fuel ratio detecting device according to claim 2, wherein said engine operating parameters comprise engine load data.

7. An air-fuel ratio detecting device according to claim 6, wherein pressure data derived based on the engine load data correspond to said second pressure.

8. An air-fuel ratio detecting device according to claim 6, wherein said engine parameters comprise atmospheric pressure data and said second pressure is derived based on the engine load data and said atmospheric pressure data.

9. An air-fuel ratio detecting device according to claim 8, wherein said second pressure is derived by adding pressure data which are obtained from the engine load data and the atmospheric pressure data.

10. An air-fuel ratio detecting device according to claim 6, wherein said operating status data detecting means comprises an inlet air sensor and an engine speed sensor so as to obtain the engine load data.

11. An air-fuel ratio detecting device according to claim 6, wherein said engine operating parameters comprise engine speed data.

12. An air-fuel ratio detecting device according to claim 11, wherein pressure data obtained based on the engine load data and the engine speed data correspond to said second pressure.

13. An air-fuel ratio detecting device according to claim 11, wherein engine torque data are derived based on the engine load data and the engine speed data, and said second pressure is derived based on the engine torque data and the engine speed data.

14. An air fuel ratio detecting device according to claim 13, wherein said engine operating parameters comprise atmospheric pressure data, the engine torque data are derived based on the engine load data and the engine speed data, and the pressure data based on the engine torque data are added to the atmospheric pressure data so as to derive said second pressure.

15. An air-fuel ratio detecting device according to claim 6, wherein said engine operating parameters comprise atmospheric pressure data, and said second pressure is derived based on the engine load data, the engine speed data and the atmospheric pressure load.

16. A method for detecting an air-fuel ratio, comprising the steps of:

(a) producing air-fuel ratio information from an air-fuel ratio sensor indicative of the concentration of oxygen in an exhaust gas produced by a burned air-fuel mixture in an internal combustion engine, said air-fuel ratio sensor being disposed in an exhaust pipe;

(b) detecting engine operating parameters indicative of or corresponding to a pressure in said exhaust gas;

(c) calculating the pressure difference between a first pressure which acts on said air-fuel ratio sensor to cause said air-fuel ratio sensor to have reference output characteristics when said air-fuel ratio sensor is placed in a reference atmosphere and a second pressure which is indicative of or corresponding to said pressure in said exhaust gas detected at said step (b); and (d) correcting an initial air-fuel ratio based on said air-fuel ratio information from said air-fuel ratio sensor with the pressure difference calculated at said step (c) to thereby produce a pressure-corrected air-fuel ratio.

17. A method according to claim 16, wherein said air-fuel ratio sensor mainly diffuses the exhaust gas with minute holes.

18. A method according to claim 17, wherein said step (b) comprises the step of detecting pressure information indicative of the exhaust pressure by a pressure sensor.

19. A method according to claim 18, wherein said air-fuel ratio sensor is disposed in the exhaust pipe so as to directly detect the exhaust pressure, and wherein the pressure information obtained by said pressure sensor corresponds to said second pressure.

20. A method according to claim 18, wherein said pressure sensor comprises an atmospheric pressure sensor for detecting an atmospheric pressure, and the atmospheric pressure obtained by said atmospheric pressure sensor corresponds to said second pressure.

21. A method according to claim 17, wherein said engine operating parameters comprise engine load data.

22. A method according to claim 21, wherein pressure data derived based on the engine load data correspond to said second pressure.

23. A method according to claim 21, wherein said engine operating parameters comprise atmospheric pressure data and said second pressure is derived based on the engine load data and said atmospheric pressure data.

24. A method according to claim 23, wherein said second pressure is derived by adding pressure data which are obtained from the engine load data and the atmospheric pressure data.

25. A method according to claim 21, wherein said step (b) obtains the engine load data by an inlet air sensor and an engine speed sensor.

26. A method according to claim 21, wherein said engine operating parameters comprise engine speed data.

27. A method according to claim 26, wherein pressure data obtained based on the engine load data and the engine speed data correspond to said second pressure.

28. A method according to claim 27, wherein said engine operating parameters comprise atmospheric pressure data, and said second pressure is derived based on the engine load data, the engine speed data and the atmospheric pressure data.

29. A method according to claim 26, wherein engine torque data are derived based on the engine load data and the engine speed data, and said second pressure is derived based on the engine torque data and the engine speed data.

30. A method according to claim 29, wherein said engine operating parameters comprise atmospheric pressure data, the engine torque data are derived based on the engine load data and the engine speed data, and the pressure data based on the engine torque data are added to the atmospheric pressure data so as to derive said second pressure.

* * * * *